(12) United States Patent
Pond

(10) Patent No.: US 8,506,293 B2
(45) Date of Patent: Aug. 13, 2013

(54) ULTRASONIC ENDODONTIC DENTAL IRRIGATOR

(76) Inventor: Gary J. Pond, Racine, WI (US)

( * ) Notice: Subject to any disclaimer, the term of this patent is extended or adjusted under 35 U.S.C. 154(b) by 0 days.

(21) Appl. No.: 11/320,286

(22) Filed: Dec. 28, 2005

(65) Prior Publication Data

US 2007/0148615 A1    Jun. 28, 2007

(51) Int. Cl.
*A61C 5/02*    (2006.01)

(52) U.S. Cl.
USPC .............................. 433/81; 433/119

(58) Field of Classification Search
USPC ................. 433/80, 81, 86, 88, 119, 77
See application file for complete search history.

(56) References Cited

U.S. PATENT DOCUMENTS

| | | |
|---|---|---|
| 611,136 A | 9/1898 | Mason |
| 1,672,114 A | 6/1928 | Crow |
| RE21,187 E | 8/1939 | Hooper |
| 2,214,230 A | 9/1940 | Freeburg |
| 2,557,222 A | 6/1951 | Goode |
| 2,711,586 A | 6/1955 | Groves |
| 2,756,740 A | 7/1956 | Deane |
| 2,812,765 A | 11/1957 | Tofflemire |
| 2,929,510 A | 3/1960 | Penn |
| 2,985,285 A | 5/1961 | Riddle |
| 3,164,153 A | 1/1965 | Zorzi |
| 3,208,145 A | 9/1965 | Turner |
| 3,593,423 A | 7/1971 | Jones |
| 3,624,907 A | 12/1971 | Brass et al. |
| 3,640,304 A | 2/1972 | Fox et al. |
| 3,645,497 A | 2/1972 | Nyboer |
| 3,718,973 A | 3/1973 | Slater et al. |
| 3,727,310 A | 4/1973 | Baker |
| 3,757,421 A | 9/1973 | Kraft |
| 3,778,903 A * | 12/1973 | Gardella et al. ............... 433/28 |
| 3,809,977 A | 5/1974 | Balamuth et al. |
| 3,874,083 A | 4/1975 | Buckley |
| 3,971,375 A | 7/1976 | Hill |
| 3,972,121 A | 8/1976 | Nash |
| 4,106,198 A | 8/1978 | Childress |
| 4,215,476 A | 8/1980 | Armstrong |
| 4,227,878 A | 10/1980 | Lohn |
| 4,253,831 A | 3/1981 | Eaton, II |
| 4,340,365 A | 7/1982 | Pisanu |
| 4,353,694 A | 10/1982 | Pelerin |
| 4,397,640 A | 8/1983 | Haug et al. |
| 4,428,748 A * | 1/1984 | Peyman et al. ............... 604/22 |
| 4,526,573 A | 7/1985 | Lester et al. |
| 4,552,531 A | 11/1985 | Martin |
| 4,578,055 A | 3/1986 | Fischer |
| 4,680,026 A | 7/1987 | Weightman et al. |
| 4,725,232 A * | 2/1988 | Hatakeyama ............... 433/98 |
| 4,762,150 A | 8/1988 | Kokuryu |
| D302,586 S | 8/1989 | Zogg et al. |
| 4,872,837 A | 10/1989 | Issalene et al. |

(Continued)

*Primary Examiner* — Sunil K Singh
(74) *Attorney, Agent, or Firm* — Ryan Kromholz & Manion, S.C.

(57) ABSTRACT

An endodontic irrigating system that is capable of using ultrasonic energy for the treatment of a root canal and other dental areas. The system has at least one and preferably multiple solution reservoirs. The reservoirs are connected to one or more handpieces, which have at least one fluid outlet. The handpiece has at least one control mechanism disposed upon the handpiece for selective delivery of fluids to the dental. Ultrasonic energy is available within the system to be used in connection with another handpiece or handpieces concurrently with fluid flow to the handpiece, such as flow of irrigating fluids.

8 Claims, 5 Drawing Sheets

(56) References Cited

U.S. PATENT DOCUMENTS

| | | | | |
|---|---|---|---|---|
| 4,915,135 | A | 4/1990 | Kellenbarger et al. | |
| 5,044,953 | A | 9/1991 | Sullivan | |
| 5,052,927 | A | 10/1991 | Discko, Jr. | |
| 5,061,180 | A | 10/1991 | Wiele | |
| 5,087,198 | A | 2/1992 | Castellini | |
| 5,171,146 | A | 12/1992 | Guerci | |
| 5,180,363 | A * | 1/1993 | Idemoto et al. | 604/22 |
| 5,199,604 | A | 4/1993 | Palmer et al. | |
| 5,204,004 | A | 4/1993 | Johnston et al. | |
| 5,230,704 | A | 7/1993 | Moberg et al. | |
| 5,234,338 | A | 8/1993 | Young | |
| 5,236,356 | A | 8/1993 | Davis et al. | |
| 5,289,919 | A | 3/1994 | Fischer | |
| 5,378,149 | A | 1/1995 | Stropko | |
| 5,378,150 | A | 1/1995 | Harrel | |
| 5,402,821 | A | 4/1995 | Harstad | |
| 5,419,772 | A | 5/1995 | Teitz et al. | |
| 5,468,148 | A | 11/1995 | Ricks | |
| 5,474,450 | A | 12/1995 | Chronister | |
| 5,526,841 | A | 6/1996 | Detsch et al. | |
| 5,554,026 | A | 9/1996 | Van Hale | |
| 5,556,279 | A | 9/1996 | Wolf et al. | |
| 5,592,974 | A | 1/1997 | Grobs et al. | |
| 5,593,304 | A | 1/1997 | Ram | |
| 5,658,144 | A | 8/1997 | Tinder et al. | |
| 5,716,210 | A | 2/1998 | Novak | |
| 5,772,433 | A | 6/1998 | Esrock | |
| 5,837,204 | A | 11/1998 | Prevost et al. | |
| 5,853,290 | A * | 12/1998 | Winston | 433/86 |
| 5,876,201 | A | 3/1999 | Wilson et al. | |
| 5,899,692 | A | 5/1999 | Davis et al. | |
| 5,927,977 | A * | 7/1999 | Sale et al. | 433/86 |
| 5,947,729 | A * | 9/1999 | Bell | 433/98 |
| 6,119,728 | A | 9/2000 | Seidel-Peschmann et al. | |
| 6,149,429 | A | 11/2000 | Bukowski et al. | |
| 6,238,211 | B1 | 5/2001 | Esrock | |
| 6,241,520 | B1 | 6/2001 | Gofman et al. | |
| 6,390,815 | B1 * | 5/2002 | Pond | 433/80 |
| 6,419,485 | B1 * | 7/2002 | Pond | 433/80 |
| 6,450,810 | B1 | 9/2002 | Fischer et al. | |
| 6,464,498 | B1 * | 10/2002 | Pond | 433/81 |
| 6,510,970 | B2 | 1/2003 | McLean et al. | |
| 2003/0077552 | A1 * | 4/2003 | Decosterd et al. | 433/84 |
| 2004/0059197 | A1 * | 3/2004 | Yamashita et al. | 600/300 |
| 2004/0072123 | A1 | 4/2004 | Simonton et al. | |
| 2005/0227201 | A1 * | 10/2005 | Pond | 433/119 |
| 2006/0269900 | A1 * | 11/2006 | Paschke et al. | 433/119 |
| 2007/0250098 | A1 * | 10/2007 | Malackowski et al. | 606/170 |

* cited by examiner

ULTRASONIC ENDODONTIC DENTAL IRRIGATOR

BACKGROUND OF THE INVENTION

The present invention relates to dental devices and equipment and more specifically to endodontic dental devices for irrigating and treating root canals and other dental surfaces.

When performing endodontic treatments, care needs to be taken to adequately prepare the root canal for the treatment or procedure. The root canal should be thoroughly debrided to remove and reduce the number of organisms within the root canal and, also, to properly shape the root canal.

Because of the intricate nature and shape of a root canal, cleaning and treatment of the root canal can become a tedious task. Conventional rotary and hand-held instruments have not been able to reach all of the small areas within the root canal. To overcome these deficiencies, devices have been designed that incorporate ultrasonic energy into the irrigating needle used in connection with the instrument for root canal debridement.

While such needles have been shown to increase the efficiency of root canal treatment processes, there is still room for improvement. Specifically, such ultrasonic powered needles have not been adequately incorporated into endodontic irrigation equipment. Irrigation equipment and devices were separately used and designed from the debridement devices. Thus, while the devices potentially could improve root canal processes, the ultrasonic systems have been separate devices from the endodontic systems. The extra equipment may make it hard to navigate while performing a dental procedure. It would be advantageous to provide tools and equipments that would incorporate and include both irrigation and debridement instruments into a single system, with the capability of ultrasonic energy being available. Such a device would allow for more efficient dental processes, both in time and how the operation is performed.

SUMMARY OF THE INVENTION

The present invention comprises an endodontic irrigating system that is capable of using ultrasonic energy for the treatment of a root canal and other dental areas. The system comprises at least one and preferably multiple solution reservoirs. The reservoirs are connected to one or more handpieces, which have at least one fluid outlet. The handpiece has at least one control mechanism disposed upon the handpiece for selective delivery of fluids to the dental. Ultrasonic energy is available within the system to be used in connection with another handpiece or handpieces concurrently with fluid flow to the handpiece, such as flow of irrigating fluids.

DESCRIPTION OF THE PREFERRED EMBODIMENT

Figure 1:
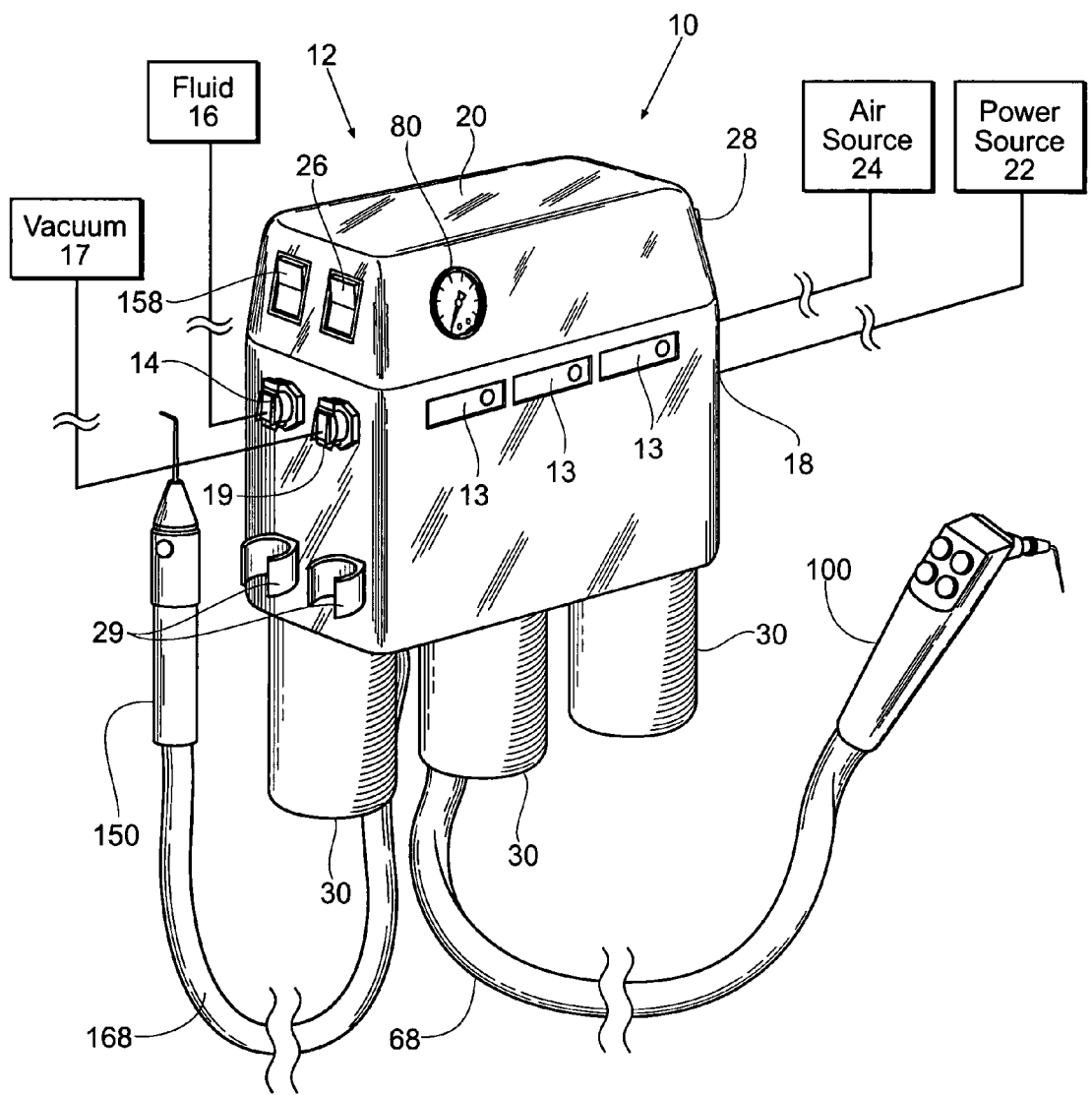
FIG. 1 is a partial perspective view of a fluid dispensing assembly according to the present invention.

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

It is to be noted that like elements are referred to with like reference numerals.

The term "fluid," as used herein, shall be defined as a gas including air, a liquid, a substance which flows, or a substance which differs from a solid in that it can offer no permanent resistance to change of shape. It shall further include mixtures of gases, mixtures of liquids, and mixtures of gases and liquids.

The invention includes a housing, at least one fluid reservoir, a fluid reservoir manifold, a fluid handpiece, an ultrasonic handpiece, and a fluid pressurizing mechanism. The ultrasonic handpiece allows for the use of ultrasonic energy during endodontic and irrigation processes.

Figure 2:
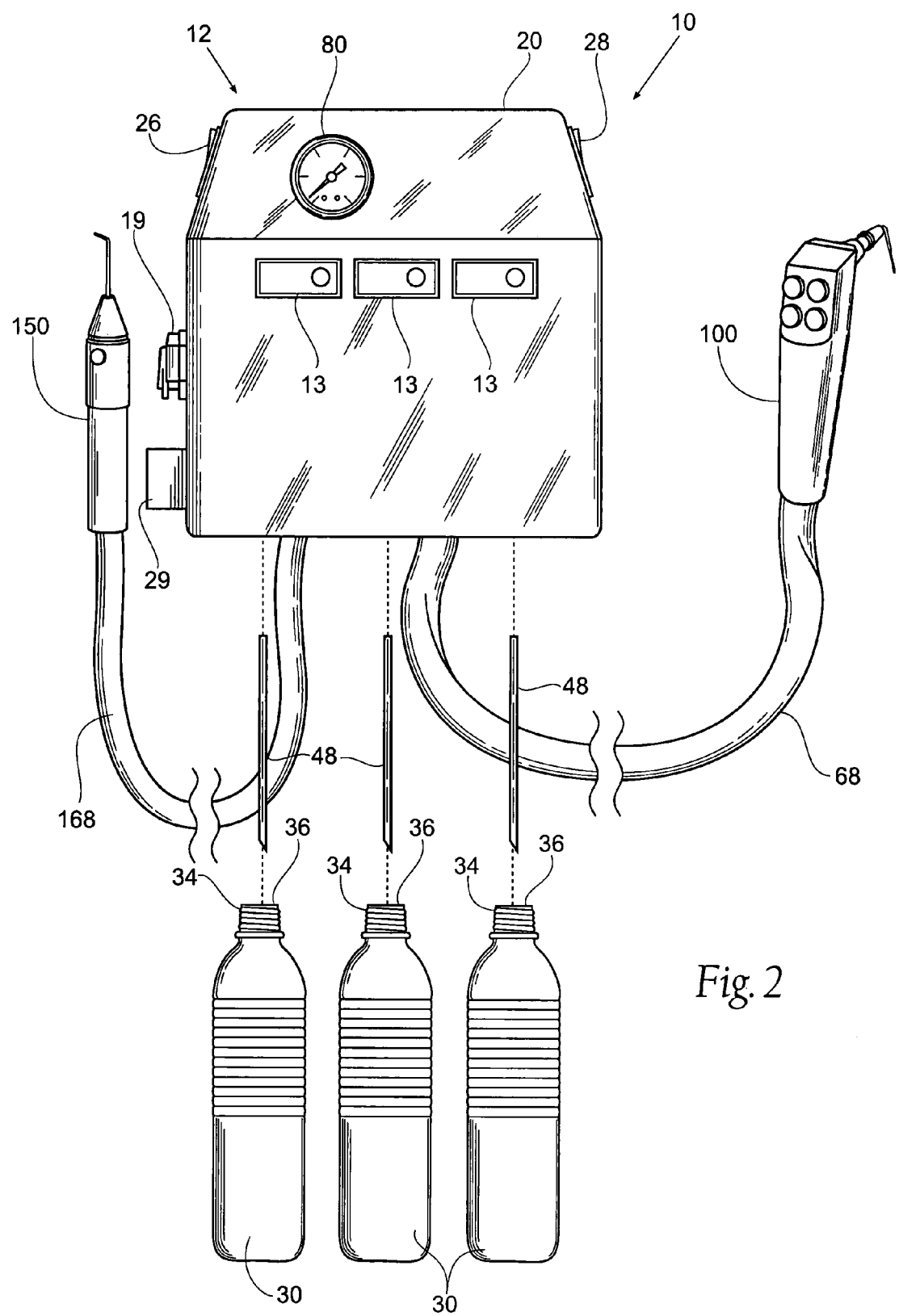
FIG. 2 is a front elevation view of the fluid dispensing assembly of FIG. 1, with certain of the components being shown in exploded relationship.

FIGS. 1 and 2 show a fluid dispensing assembly 10 in accordance with the present invention. The assembly 10 dispenses fluid from a fluid supply system 12 to a dental handpiece 100, with the system 12 generally comprising a housing 20, which supports at least one fluid reservoir 30. The assembly 10 also provides ultrasonic energy to an ultrasonic dental tool 150, preferably an ultrasonic scaler 150. The ultrasonic power may be delivered to the ultrasonic handpiece 150 concurrently while using the handpiece 100 during normal endodontic procedures.

The housing 20 may be of any preferred size or shape. The housing 20 supports a display 13 or displays 13 for viewing the fluid levels of the reservoirs 30. The display 13 may also include a LED or other indicators to determine which of the reservoirs 30 is being accessed by the dental handpieces 100 and 150. The housing 20 also supports a fluid port 14 that allows the assembly to be connected to a fluid source 16, most preferably a water source. A vacuum source 17 is connected to the housing 20 by a vacuum port 19. The assembly 10 may have an outlet 18 that allows the assembly 10 to be in communication with an external power source 22. The assembly 10 may be connected to an external air source 24. The assembly 10 may further comprise a main power switch 26 and a heater switch 28. Also the housing 20 can support a plurality of instrument holders 29 for supporting the handpieces 100 and 150 when not in use, and the housing 20 may have additional holders 29 for other handpieces.

Figure 3:
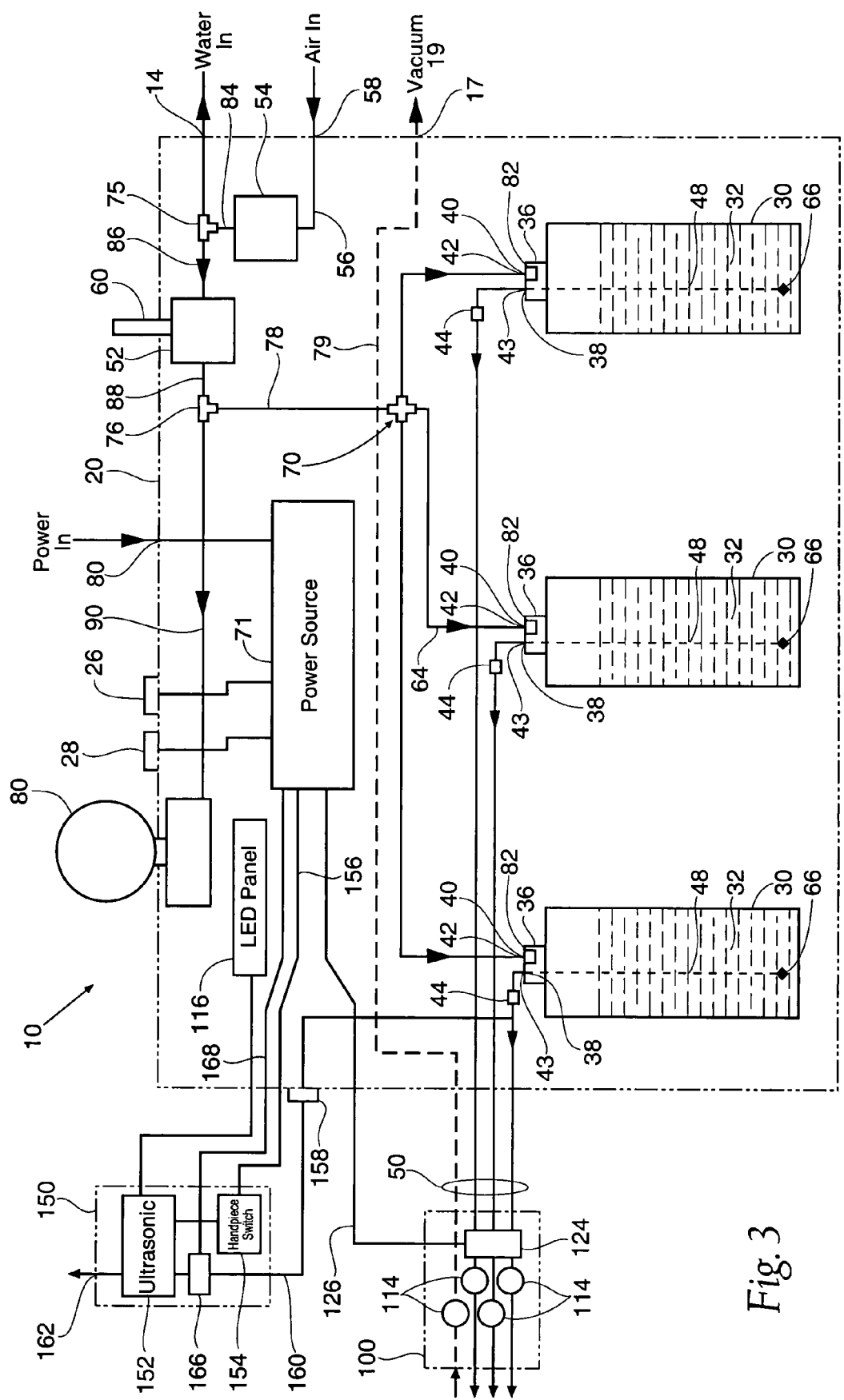
FIG. 3 is a schematic view of the fluid dispensing assembly of FIG. 1.
Figure 4:
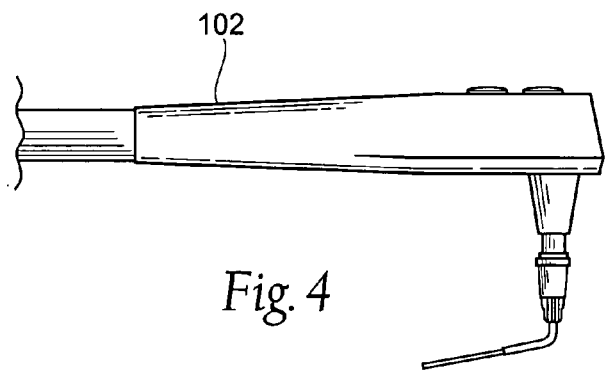
FIG. 4 is a fragmentary, side elevation view of a handpiece used with the fluid dispensing assembly.
Figure 5:
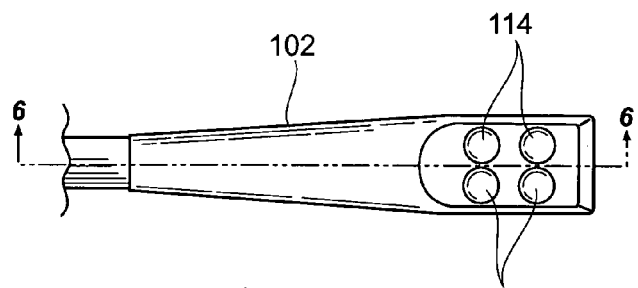
FIG. 5 is a fragmentary, top plan view of the handpiece of FIG. 4.

The reservoir or reservoirs 30 are capable of containing fluid 32 (see FIG. 3). The reservoir or reservoirs 30 are carried by the housing 20. It is apparent that any number of reservoirs could be utilized depending on the preferences of an individual. For illustration, three reservoirs 30 are shown. The reservoir 30 can come in many forms, including, for example, a bottle, a canister, a dual-compartment bottle or canister; and can range greatly in size. Preferably, however, the reservoir 30 is an inexpensive clear plastic bottle with an engageable neck 34 (see FIG. 2), similar to a common water bottle with the cap removed. As shown, the reservoirs can be of varying sizes, depending on the specific fluid that the reservoir 30 houses. Reservoirs of this type are readily available from a variety of sources and manufacturers, and are most commonly available in a 10-20 fluid ounce capacity size. The clear bottle allows for a determination of the amount of fluid 32 remaining in the reservoir 30, and a reservoir of this type is capable of withstanding internal pressure, though typically the resistance to pressure for this type of reservoir is limited to approximately 50 pounds per square inch (psi). Although a stronger reservoir is capable of use with the fluid supply system, such as a high density polyethylene reservoir, the polyethylene terephthalate elastomer (PETE) construction common to plastic soda and water bottles provides sufficient rigidity, is easily available, and is inexpensive.

Referring now to FIG. 2, the reservoir 30 is detachably coupled to a reservoir head 36 (hidden from view in FIG. 1). The reservoir head 36 is designed to provide the reservoir 30 with an air-tight seal capable of containing pressures up to 50 psi, but higher pressures are capable with different reservoir embodiments. The detachable coupling may be provided by a threaded neck 34 on the reservoir 30 and a female thread on the reservoir head 36. However, it is to be understood that a variety of means for removably coupling each reservoir 30 to the reservoir head 36 may be employed. The detachable coupling allows for quick and simple reservoir changes, should refills or different fluids be desired for use with the fluid dispensing assembly 10.

The reservoir head 36 has two fluid passageways or two communicative conduits 38 and 40 indicated schematically on FIG. 3, between the reservoir 30 and the remainder of the fluid dispensing assembly 10 and fluid supply system 12. The first communicative conduit provides a pathway to the interior of the reservoir 30 for pressurized air through an air inlet fitting 42. The second communicative conduit 38 is a fluid outlet fitting 43, providing a fluid passage for fluid to leave the reservoir 30.

The ultrasonic handpiece 150 comprises an ultrasonic transducer 152 that is connected to a control switch 154, which is connected to a power source 71 by a power line or wire 156. The ultrasonic handpiece 150 is further coupled to at least one of the fluid reservoirs 30. As an example and not as a limitation, FIG. 3 shows the ultrasonic handpiece 150 coupled to one reservoir 30. A fluid control switch 158 allows the operator to control fluid flow from the reservoir 30 through a fluid line 160 to an outlet 162 of the ultrasonic handpiece 150. The control switch 158 is preferably located on the housing 20, but could be located on the handpiece 150, if desired.

It is conventional to supply sodium hypochlorite during certain dental procedures to either irrigate, debride and disinfect the mouth of a patient, or to destroy bacteria present in the dental unit water line. The components of the fluid supply system 10 that come into contact with the sodium hypochlorite are preferably constructed of material capable of withstanding the corrosive effects of the sodium hypochlorite. These components, as shown in FIGS. 1-7, inclusive, include a check valve 44, a fluid draw line 48, a fluid outlet line 50, the fluid outlet fitting 43, the reservoir 30, the reservoir head 36, and the handpiece 100, and are preferably constructed of sodium hypochlorite resistant material. Likewise, the ultrasonic handpiece 150 and the related elements of the ultrasonic handpiece 150 are also preferably constructed of sodium hypochlorite resistant material. Because sodium hypochlorite is particularly corrosive with respect to metal, non-metal components are preferred. Plastic is a preferred construction material because of its resistance to sodium hypochlorite corrosion. The fluid outlet lines 50 preferably have an inner layer and an outer layer, the inner layer preferably being constructed of polyethylene (PE) and the outer layer preferably being constructed of polyvinyl chloride (PVC).

Dental offices are often unique with respect to the air pressure in the air system. Dental offices operate at higher or lower pressures based on operator preference, the output of the air compressor, the number of components in the office using air, and the number of components in use at any one time. For this reason, the fluid supply system 10 is supplied with an adjustable air pressure regulator 52 and a fixed air pressure regulator 54. Adjustable air pressure regulator 52 is coupled with an air supply line 56 and the a tee fitting 70 between an air inlet 58 and the reservoir 30, as is best shown in FIG. 3. This arrangement avoids erratic and uncontrollable fluid flow from the fluid supply system 10 and ultimately the handpiece 100. Preferably, pressure in the adjustable air pressure regulator 52 is adjustable by operation of an air pressure regulator adjuster 60, according to the operator's preference, who has the capability to alter the air pressure to provide a consistent output of fluid.

As previously stated and as shown in FIGS. 1 and 2, the pressurized air is conveyed from a conventional source of pressurized air common in dental offices, through the air supply line 56 coupled with the source of pressurized air in any general fashion as is known in the art. The air supply line 56 is ultimately communicatively coupled with the inlets 42 of the reservoirs 30 and their respective reservoir head 36. Each air supply line 64 leads to the air inlet fitting 42 to supply pressurized air to the reservoir 30.

The pressurized air is supplied to force fluid 32 from the reservoir 30 through a distal end 66 of the fluid draw line 48 through the fluid outlet fitting 43 and through the fluid outlet lines 50, contained within an outlet line sheath 68, and ultimately to components of the handpiece 100.

As further disclosed in FIG. 3, a tee fitting 70 is used to disperse pressurized air to each of the reservoirs 30. The fitting 70 receives pressurized air from the air supply line 56 passing through the adjustable air pressure regulator 52 to a tee-fitting 76, where one port supplies air to an air line 78. The other port of the tee-fitting 76 being in communication with a pressure gauge 80. The pressurized air delivered through the fitting 70 through hydrophobic filters 82 and to individual air inlet fittings 42 on the reservoir heads 36, thus pressurizing the fluid 32 and forcing the same through the fluid draw lines 48 to the fluid outlet lines 50 and through check valves 44. As will be described later, the fluid outlet lines 50 communicate with the handpiece 100. The hydrophobic filter 82 is disclosed schematically in FIG. 3.

As shown in FIG. 3, the present embodiment further contemplates the use of separate common tee—fittings 75 and 76. Here, the air supply line 56 enters the fluid supply system 10, and the air supply line 56 is split by a first common tee fitting 75 to split the air passage into two distinct pathways. One pathway 84 leads to the adjustable air pressure regulator 52 from the fixed air pressure regulator 54. Another pathway 86 for air travel leads to the fixed air pressure regulator 54. Preferably, the first common tee fitting 75 may be used to split the air flow into two distinct pathways.

Air enters the fixed air pressure regulator 52 through air supply line 56. Leaving the adjustable air pressure regulator 52, an air outlet line 88 is split by the second common tee-fitting 76 to split the air passage into two distinct pathways. As shown on FIG. 3, one pathway 90 leads to the pressure gauge 68. Another pathway 78 leads to the fitting 70.

The vacuum source 17, which is connected to the housing 20 by the vacuum port 19, is directly connected to the handpiece 100 by the conduit 79. The handpiece 100 is then capable of selectively acting as a suction or vacuum device.

Referring to FIGS. 2 and 3, the fluid draw line 48 is coupled to the apertured fluid outlet fitting 43 located on the underside of reservoir head 36. The fluid draw line 48 is sized to extend from the top of the reservoir 30 to a point which is near the bottom of the reservoir, so that the fluid supply system 10 can operate until the reservoir 30 is nearly empty of fluid 32. The fluid outlet line 50 is communicatively coupled with the fluid outlet fitting 43 on the upper side of the reservoir head 36, extending the pathway for fluid 32 leaving the reservoir 30. The previously mentioned hydrophobic filter 82 is seated within a through bore communicating at the underside of reservoir head 36 as shown in FIG. 3.

Alternatively, the fluid draw line 48 and the fluid outlet line 50 could be integrated into a single line serving the same purpose of providing a conduit for fluid 32 to leave the reservoir 30 and retain pressure within the reservoir 30, if an air-tight fitting around the line is used as opposed to fluid outlet fitting 43. However, the use of both the fluid draw line 48 and the fluid outlet line 50 is preferred, mainly because this arrangement provides a better pressure seal than a single line with an air-tight fitting around the line. Each fluid outlet line 50 includes the check valve 44 coupled with the fluid outlet line 50, in order to prevent fluid 32 from flowing back into the reservoir 30.

A plurality of fluid outlet lines 50 emerge from the fluid supply system 10, (see FIG. 3) and enter a distal end of the outlet line sheath 68 (see FIGS. 1 and 2). The vacuum conduit 79 also enters the sheath 68. The sheath 68 is preferably flexible, allowing ease of mobility during treatment of the patient, but also rigid enough to withstand penetration, line puncture, and kinking. The sheath 68 may be detachably coupled to a distal end of a handpiece handle 102 by a threaded couple (not shown), and the sheath 68 may be detachably coupled to a fluid reservoir manifold 92 (see FIG. 8) by a similar threaded couple. After entering the distal end of the sheath 68, the fluid outlet lines 50 extend a predetermined distance from the distal end of the sheath and exit a proximal end of the sheath 68. The length of the sheath 68 and fluid outlet lines 50 is primarily determined by the distance between the fluid supply system 12 and the patient. Subsequently, the fluid outlet lines 50 enter a handpiece manifold 104 disposed within the handpiece handle 102, and the fluid outlet lines 50 are coupled with a plurality of respective fluid inlets 106 within the handpiece manifold 104. Also disposed within the handpiece handle 102 is a single fluid discharge line 108, through which a selected fluid passes into before being delivered into the patient's mouth.

The power line 156 and the fluid line or lines 160 leading from the assembly 10 to the ultrasonic handpiece 150 are housed within a second sheath 168, similar to the sheath 68 used in connection with the endodontic handpiece 100. The second sheath 168 can be connected to the assembly 10 similarly as described for the sheath 68, and the length of the second sheath 168 can also be designed for needs as described for the sheath 68, above.

Referring to FIGS. 4-6B, inclusive, in order for the operator to select which fluid 32 to use, a momentary switch or switches 114, such as a membrane switch, is provided on the handpiece 100 to actuate flow of a specific fluid to a dental tip 120. Depression of the proper momentary switch allows quick supply of fluid 32 from the proper reservoir 30 through a fluid intake line 106 to the fluid outlet 108. Alternatively, a single switch 114 may be used and selection of the proper reservoir may happen somewhere other than on the handpiece 100. The dental tip 120 may be coupled to the handpiece 100 by a coupling device or adaptor 122. Pressure may be delivered to the particular reservoir 30 containing the selected fluid 32, allowing the operator to quickly supply the desired fluid following a depression of the momentary switch 114, as opposed to having to wait for the air supply to re-pressurize the reservoir 30 with each alternation in fluid. In this arrangement, only one reservoir 30 is pressurized at a time. Either arrangement or other similar arrangements that allow selective delivery of fluid would fall under the scope of the present invention.

Figure 6A:
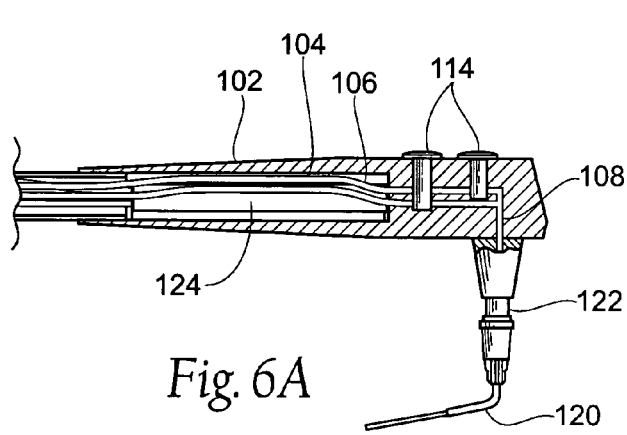
FIG. 6A is a sectional view of the handpiece of FIG. 4.
Figure 6B:
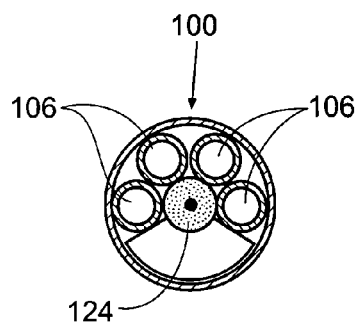
FIG. 6B is a cross-sectional view of the handpiece of FIG. 6A

As shown in FIG. 6B, the handpiece 100 also has a heating element 124 for heating the fluid lines 106 before they exit the fluid discharge line 108. The heating element 124 is connected to the power source 71 by a heating wire 126 (see FIG. 3). The heater switch 28 controls whether heat is supplied to the heating element. The arrangement shown in FIG. 6B is only one possible arrangement for heating the fluids and should not be considered limiting as to the scope of the heating device. For instance, each of the fluid lines could be heated separately, or the heating element could be located within the housing 20. Alternatively, the system 10 may be designed without a heating element.

Figure 7:
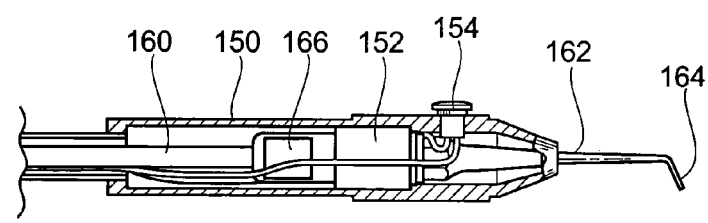
FIG. 7 is a fragmentary, side sectional view of an ultrasonic handpiece used with the fluid dispensing assembly of the present invention.

FIG. 7 provides a view of the ultrasonic dental handpiece 150. Depression of the fluid control switch 158 allows fluid to pass from one of the reservoirs 30 that is coupled to the handpiece 150 to the fluid outlet 162 and to the dental tip 164. This is done while ultrasonic energy is also delivered to the dental tip 164 through the ultrasonic transducer 152. Fluid passes through the supply line 160, through the transducer 152, before exiting the dental tip 164. As previously noted with respect to FIG. 3, the fluid switch 158 for the handpiece 150 is located on the housing 20. When the fluid switch 158 is turned off, the handpiece 150 may still operate as an ultrasonic handpiece 150. The handpiece 150 may also be used concurrently with the handpiece 100, as operations dictate.

As with the handpiece 100, the ultrasonic handpiece 150 may also have a heating element 166 located within the handpiece 150. The heating element 166 is connected to the power source by a heating wire 168. The heating element 166 could also be controlled by the heating switch 28. Alternatively, the individual heating switches could be used for the heating elements 124 and 168. Likewise, as described above with respect to the heating element 124, the heating element could be placed in different areas within the assembly 10, or not be used at all.

Figure 8:
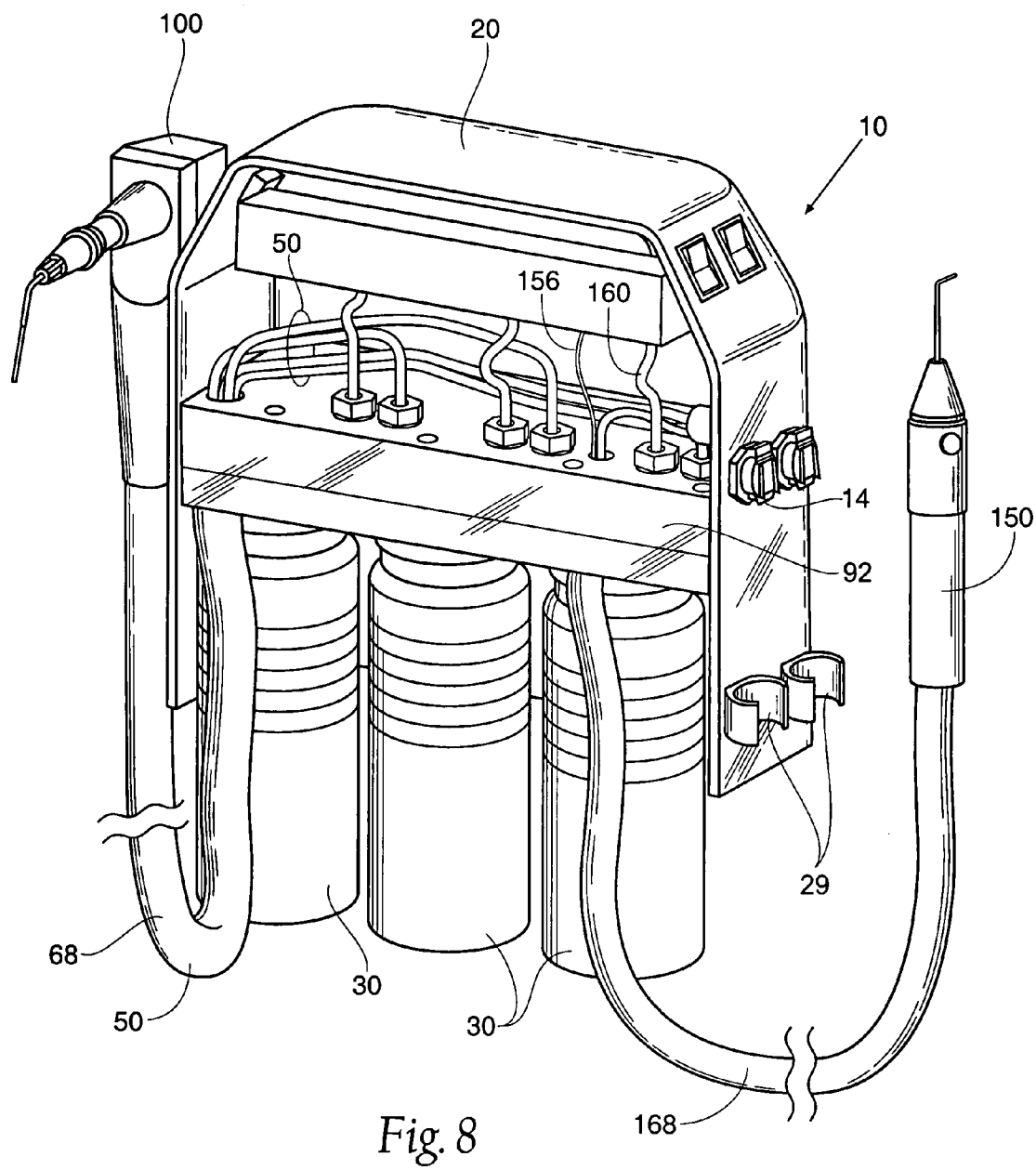
FIG. 8 is a rearward partially perspective view of the fluid dispensing assembly of the present invention.

FIG. 8 shows a rear perspective view of the system 10. As previously described, the fluid outlet lines 50 pass through the fluid reservoir manifold 92 into the outlet line sheath 68 and are in fluid communication with the handpiece 100. Similarly the fluid outlet 160 and the power line 156 pass through the manifold 92 into the sheath 168 and are in fluid communication with the handpiece 150. It is understood that more or fewer reservoirs 30 may be connected to either of the handpieces 100 and 150 and the arrangement would still fall within the present invention.

The present invention is unique in that it provides both endodontic and ultrasonic handpieces within the same housing, which allows a dentist more flexibility during dental operations. While the device is shown having a single endodontic handpiece and a single ultrasonic handpiece, there could be more handpieces than show and still fall within the scope of the present invention.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. An irrigation system for dispensing a liquid, said system comprising:
    a housing;
    a plurality of liquid reservoir supported by said housing;
    a handpiece in selectable communication with at least one of said liquid reservoirs, said handpiece having at least one liquid outlet;
    a control mechanism located on said handpiece for controlling flow of liquid to said liquid outlet from said liquid reservoir;
    a second handpiece, said second handpiece being an ultrasonic handpiece, said ultrasonic handpiece coupled independently of said first handpiece to said housing, said ultrasonic handpiece comprising an ultrasonic transducer, said ultrasonic handpiece in fluid communication with at least one of said liquid reservoirs;
    an ultrasonic energy source located in said housing, said ultrasonic energy source connected to said ultrasonic handpiece; and
    a second control mechanism for controlling delivery of ultrasonic energy to said ultrasonic handpiece;
    a third control mechanism for controlling delivery of liquid from one of said liquid reservoirs to said ultrasonic handpiece;
    wherein said second and third control mechanisms allow for delivery of said liquid and said ultrasonic energy to said ultrasonic handpiece independently and simultaneously; and
    wherein said control mechanisms allowing for said handpiece and said second ultrasonic handpiece being capable of independently and simultaneously delivering liquid from one of said liquid reservoirs.

2. The irrigation system according to claim 1 further comprising means for pressurizing the liquid in said liquid reservoirs.

3. A dental system for providing ultrasonic energy during an endodontic dental procedure, said system comprising:
    a housing;
    a plurality of pressurized liquid reservoirs being supported by said housing;
    an endodontic handpiece having a liquid outlet and being in fluid communication with said liquid reservoirs, said endodontic handpiece comprising means for automatically selecting liquid flow from one of said liquid reservoirs to said liquid outlet;
    means for actuating said endodontic handpiece;
    an ultrasonic energy source located in said housing;
    an ultrasonic handpiece being connected to said ultrasonic energy source, said ultrasonic handpiece having a liquid outlet being in fluid communication with at least one of said liquid reservoirs;
    means for actuating said ultrasonic energy in said ultrasonic handpiece; and
    a separate means for actuating fluid flow in said ultrasonic handpiece
    control mechanisms configured to allow said endodontic handpiece and said ultrasonic handpiece to independently and simultaneously deliver liquid from one of said pressurized liquid reservoirs.

4. The dental system according to claim 3 further comprising means for regulating fluid pressure in said liquid reservoirs.

5. The dental system according to claim 3 wherein said ultrasonic handpiece is an ultrasonic scaler.

6. The dental system according to claim 3 further comprising means for heating liquid within said endodontic handpiece.

7. The dental system according to claim 3 further comprising means for heating liquid within said ultrasonic handpiece.

8. The dental system according to claim 3 further comprising means for controlling liquid flow to said ultrasonic handpiece.

* * * * *